(12) United States Patent
Roussev et al.

(10) Patent No.: US 10,180,416 B2
(45) Date of Patent: Jan. 15, 2019

(54) METHODS OF CHARACTERIZING ION-EXCHANGED CHEMICALLY STRENGTHENED GLASSES CONTAINING LITHIUM

(71) Applicant: CORNING INCORPORATED, Corning, NY (US)

(72) Inventors: Rostislav Vatchev Roussev, Painted Post, NY (US); Vitor Marino Schneider, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 188 days.

(21) Appl. No.: 15/171,490

(22) Filed: Jun. 2, 2016

(65) Prior Publication Data
US 2016/0356760 A1   Dec. 8, 2016

Related U.S. Application Data

(60) Provisional application No. 62/170,919, filed on Jun. 4, 2015.

(51) Int. Cl.
| | |
|---|---|
| G01B 11/16 | (2006.01) |
| G01N 33/38 | (2006.01) |
| C03C 21/00 | (2006.01) |
| G01L 1/00 | (2006.01) |

(52) U.S. Cl.
CPC ......... *G01N 33/386* (2013.01); *C03C 21/002* (2013.01); *G01L 1/00* (2013.01)

(58) Field of Classification Search
CPC ....... G01B 11/16; G01B 11/165; G01B 11/18; G01L 1/24; G01M 11/086

USPC .......................................................... 356/32
See application file for complete search history.

(56) References Cited

U.S. PATENT DOCUMENTS

| | | | |
|---|---|---|---|
| 8,957,374 B2 * | 2/2015 | Liu | G01J 4/04 |
| | | | 250/338.1 |
| 9,140,543 B1 * | 9/2015 | Allan | G01L 1/24 |
| 2013/0224492 A1 | 8/2013 | Bookbinder et al. | |
| 2014/0368808 A1 | 12/2014 | Roussev et al. | |
| 2015/0066393 A1 | 3/2015 | Liu et al. | |

FOREIGN PATENT DOCUMENTS

WO    2015077179 A1    5/2015

OTHER PUBLICATIONS

International Search Report and Written Opinion PCT/US2016/035449 dated Sep. 9, 2016.

* cited by examiner

*Primary Examiner* — Md M Rahman
(74) *Attorney, Agent, or Firm* — Kevin M. Johnson

(57) ABSTRACT

Methods of characterizing ion-exchanged chemically strengthened Li-containing glasses include: a) measuring a mode spectrum of the glass sample; b) using the mode spectrum, estimating a first contribution to the center tension associated with a spike region and estimating a second contribution to the center tension due to a deep region only, wherein the deep region is assumed to follow a power-law stress profile; and c) determining a total center tension by adding of the first and second contributions to the center tension. The methods can be used for quality control during manufacturing of glass samples by comparing the total center tension to a center tension specification that provides optimum strength and durability.

17 Claims, 7 Drawing Sheets

US 10,180,416 B2

METHODS OF CHARACTERIZING ION-EXCHANGED CHEMICALLY STRENGTHENED GLASSES CONTAINING LITHIUM

CROSS-REFERENCE TO RELATED APPLICATIONS

This Application claims the benefit of priority under 35 USC § 119(e) of U.S. Provisional Patent Application No. 62/170,919, filed on Jun. 4, 2015, and which is incorporated by reference herein.

FIELD

The present disclosure relates to chemically strengthened glass, and in particular relates to methods of characterizing ion-exchanged chemically glasses containing lithium.

BACKGROUND

Chemically strengthened glasses are glasses that have undergone a chemical modification to improve at least one strength-related characteristic, such as hardness, resistance to fracture, etc. Chemically strengthened glasses have found particular use as cover glasses for display-based electronic devices, especially hand-held devices such as smart phones and tablets.

In one method, the chemical strengthening is achieved by an ion-exchange process whereby ions in the glass matrix are replaced by externally introduced ions, e.g., from a molten bath. The strengthening generally occurs when the replacement ions are larger than the native ions (e.g., Na+ ions replaced by K+ ions). The ion-exchange process gives rise to a refractive index profile that extends from the glass surface into the glass matrix. The refractive index profile has a depth-of-layer or DOL that defines a size, thickness or "deepness" of the ion-diffusion layer as measured relative to the glass surface. The refractive index profile also defines a number of stress-related characteristics, including stress profile, surface stress, center tension, birefringence, etc. The refractive index profile defines an optical waveguide when the profile meets certain criteria.

Recently, chemically strengthened glasses with a very large DOL (and more particularly, a large depth of compression) have been shown to have superior resistance to fracture upon face drop on a hard rough surface. Glasses that contain lithium ("Li-containing glasses") can allow for fast ion exchange (e.g., Li+ exchange with Na+ or K+) to obtain a large DOL. Substantially power law (e.g., substantially parabolic) stress profiles are easily obtained in Li-containing glasses, where the ion-exchange concentration profile of Na+ connects in the central plane of the substrate, shrinking the traditional central zone of the depth-invariant center tension to zero or negligible thickness. The associated stress profiles have a predictable and large depth of compression, e.g., on the order of 20% of the sample thickness, and this depth of compression is quite robust with respect to variations in the fabrication conditions.

An example power law stress profile of particular commercial importance is a near-parabolic (substantially parabolic) profile for the deep region that joins to a "spike" portion near the surface. This spike portion ("spike") is particularly helpful in preventing fracture when glass is subjected to force on its edge (e.g., a dropped smart phone) or when the glass experiences significant bending. The spike can be achieved in Li-containing glasses by ion exchange in a bath containing $KNO_3$. It is often preferred that the spike be obtained in a bath having a mixture of $KNO_3$ and $NaNO_3$ so that Na+ ions are also exchanged. The Na+ ions diffuse faster than K+ ions and thus diffuse at least an order of magnitude deeper than the K+ ions. Consequently, the deeper portion (region) of the profile is formed mainly by Na+ ions and the shallow portion of the profile is formed mainly by K+ ions.

In order for chemically strengthened Li-containing glasses to be commercially viable as cover glasses and for other applications, their quality during manufacturing must be controlled to certain specifications. This quality control depends in large part on the ability to control the ion-exchange process during manufacturing, which requires the ability to quickly and non-destructively measure the refractive index (or stress) profiles.

Unfortunately, the quality control for glasses with spike stress profiles is wanting due to the inability to adequately characterize the profiles in a non-destructive manner. This inability has made manufacturing of chemically strengthened Li-containing glasses difficult and has slowed the adoption of chemically strengthened Li-containing glasses in the market.

SUMMARY

An aspect of the disclosure is directed to methods of characterizing chemically strengthened Li-containing glasses having a surface stress spike, such as produced by an ion-exchange process whereby Li+ is exchanged with K+ and Na+ ions (i.e., Li+ ⇔ K+, Na+). The methods result in a measurement of the surface compression and the depth of the spike, and its contribution to the center tension, as well as the compression at the bottom of the spike, and the total center tension.

The method is preferably carried out to obtain a commercially important stress profile. An example of such a profile follows a power law (e.g., substantially parabolic) in most of the interior ("deep region") of the substrate other than the spike region ("spike") adjacent the substrate surface. The spike is generally formed by the slower diffusion (and thus shallower) K+ ions while the power-law portion is formed by the faster (and thus deeper) diffusing Na+ ions. The method allows for confirmation that the profile has reached the power-law, e.g., has a self-consistency check. The method can also include performing quality control of the glass samples being process. Such quality control is important for a commercially viable manufacturing process.

An aspect of the method involves measuring the mode lines or fringe spectrum of the K+ spike layer of the glass sample using a prism-coupling system to calculate surface stress (CS), depth of the spike (D1=$DOL_{sp}$), and the center tension (CT) contribution of the spike. In addition, a shift of an intensity transition corresponding to index at the depth of the bottom of the spike is measured, providing an estimate of the stress at the bottom of the spike. The depth of the spike ($DOL_{sp}$) and the depth of layer (DOL) is used to verify that the rest of the profile is in the power-law regime. Then the total CT is estimated assuming that the profile is follows a power law, taking into account the CT contribution of the spike. If the profile is expected to deviate moderately from a power law, the expected deviation can be accounted for by an adjustment factor in the target CT. If necessary, the depth of compression (DOC) is also estimated, taking into account the reduction of DOC resulting from the spike, relative to the DOC of a power-law profile.

In another aspect of the method, relationship is defined between the measurement wavelength and the target properties of the Na+-enriched deeper portion of the profile to help ensure a precise measurement of the compression at the bottom of the spike, and the most precise estimate of the CT and frangibility.

In another aspect of the method, a prism-coupling measurement of the mode spectrum is combined with a measurement of the weight gain, or measurements of the sample thickness and the sample weight, to estimate the amount of Na+ diffused in the sample.

Advantages of the methods disclosed herein include that they are non-destructive and high-throughput, and can provide a measurement of critical parameters of the stress profile with high precision. These parameters include the compressive stress CS, depth of spike DOS, depth of layer DOL, center tension CT and frangibility status, which is based on the center tension CT.

Additional features and advantages are set forth in the Detailed Description that follows, and in part will be readily apparent to those skilled in the art from the description or recognized by practicing the embodiments as described in the written description and claims hereof, as well as the appended drawings. It is to be understood that both the foregoing general description and the following Detailed Description are merely exemplary, and are intended to provide an overview or framework to understand the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the Detailed Description serve to explain principles and operation of the various embodiments. As such, the disclosure will become more fully understood from the following Detailed Description, taken in conjunction with the accompanying Figures, in which.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

In the discussion below, the term "power law" refers to a function that in an example follows the general form $f(x) = ax + bx^2 + cx^3 + dx^4 \ldots$, where a, b, c and d are coefficients.

Figure 1A:
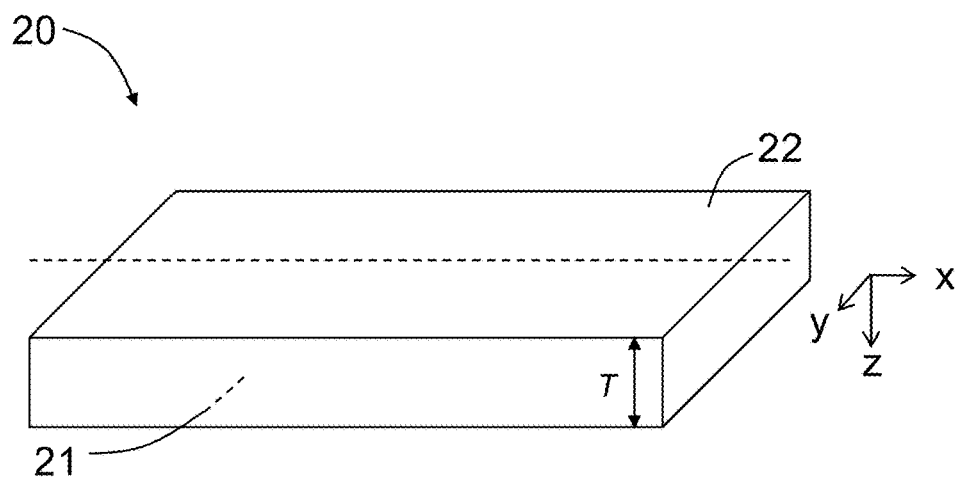
FIG. 1A is an elevated view of an example DIOX glass substrate in the form of a planar substrate.
Figure 1B:
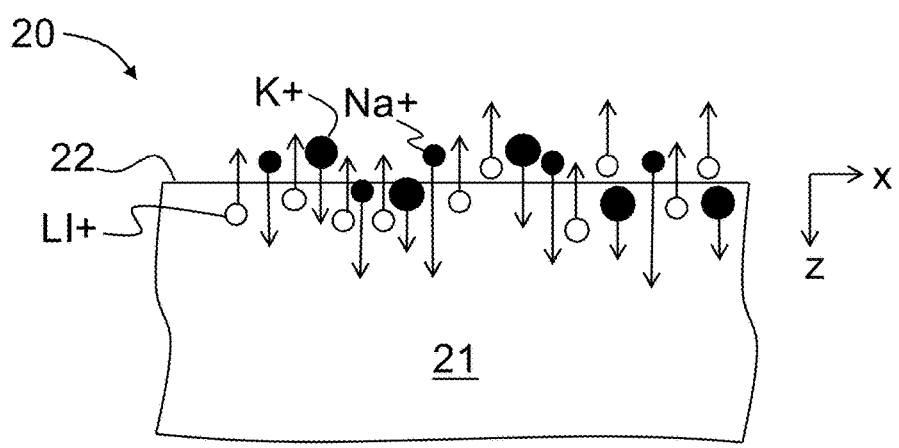
FIG. 1B is a close-up cross-sectional view of the DIOX substrate of FIG. 1A as taken in the x-z plane and that illustrates the double ion-exchange process that takes place across the substrate surface and into the body of the substrate.

FIG. 1A is an elevated view an example glass substrate in the form of a planar ion-exchanged substrate 20 that has a body 21 and a (top) surface 22, wherein the body has a base (bulk) refractive index $n_s$, a surface refractive index $n_0$ and a thickness T in the z-direction. FIG. 1B is a close-up cross-sectional view of ion-exchanged substrate 20 as taken in the y-z plane and illustrates an example double ion-exchange (DIOX) process that takes place across surface 22 and into body 21 in the z-direction.

In the DIOX process discussed in connection the method disclosed herein, two different types of ions Na+ and K+ replace another different ion Li+ that is part of the glass body 21. The Na+ and K+ ions can be introduced into the glass body 21 either sequentially or concurrently using known ion-exchange techniques. As noted above, the Na+ ions diffuse faster than the K+ ions and thus go deeper into the glass body 21. This has an effect on the resulting refractive index profile and stress profile, as discussed below.

Figure 1C:
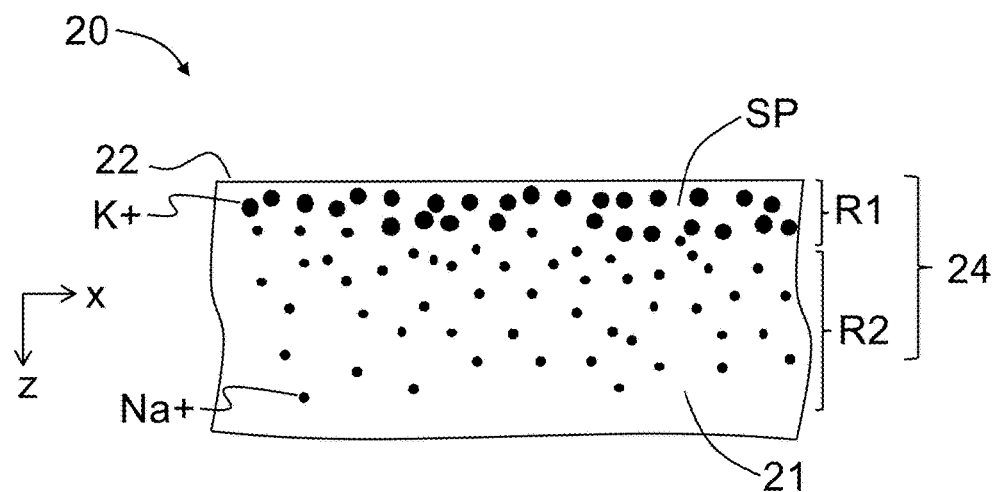
FIG. 1C schematically illustrates the result of the DIOX process that forms the DIOX substrate.
Figure 2:
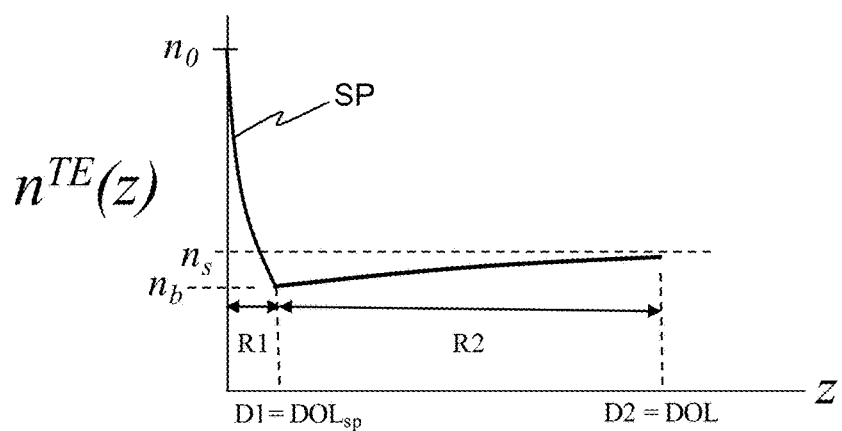
FIG. 2 is a representation of an example refractive index profile n(z) for the DIOX substrate illustrated in FIG. 1C.

FIG. 1C is a schematic diagram of the resulting DIOX process, and FIG. 2 is a representation of an example refractive index profile n(z) for substrate 20 having undergone the DIOX process and having a refractive index profile such as illustrated in FIG. 1C. The corresponding stress profile can be represented by σ(z). The refractive index profile n(z) includes a first "spike" region R1 associated with the shallower ion-exchange (K+ ions) and that has a depth D1 into body 21 that defines a "depth-of-layer for the spike" denoted hereinafter as $DOL_{sp}$. The refractive index profile n(z) also includes a second region R2 associated with the deeper ion-exchange (Na+ ions) and that has a depth D2 that defines the depth-of-layer (DOL).

The deeper second region R2 may be produced in practice prior to the shallower region. The region R1 is adjacent substrate surface 22 and is relatively steep and shallow, whereas region R2 is less steep and extends relatively deep into the substrate to the aforementioned depth D2. In an example, region R1 has a maximum refractive index $n_0$ at substrate surface 22 and steeply tapers off to an intermediate index $n_i$, while region R2 tapers more gradually from the intermediate index down to the substrate (bulk) refractive index $n_s$. The portion of the refractive index profile n(z) for region R1 represents a "spike" in the refractive index having a depth DOS.

Figure 3:
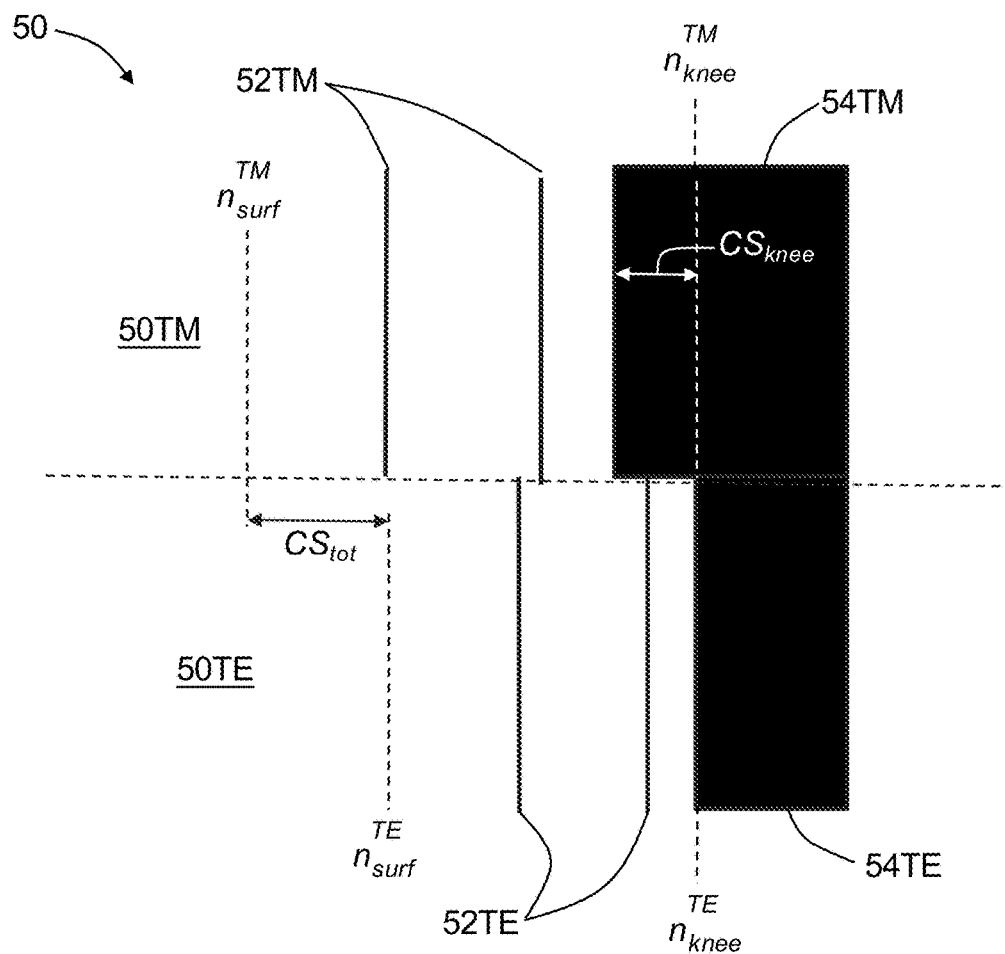
FIG. 3 is a schematic representation of an example measured mode spectrum of a Li-containing glass formed by an ion-exchange process using a mixture of $NaNO_3$ and $KNO_3$, with the mode spectrum including TM (top) and TE spectra (bottom), and also showing profile measurement parameters as explained below.

FIG. 3 is schematic representation of an example measured mode spectrum 50 of a Li-containing glass formed by an ion-exchange process using a mixture of $NaNO_3$ and $KNO_3$, with the mode spectrum including TM and TE spectra 50TM and 50TE (upper and lower portions, respectively) with respective mode lines 52TM and 52TE. The glass type is 196HLS with a fictive temperature of 638° C. The glass was subjected to a Li+ ⇔ K+, Na+ ion-exchange process by placing the glass sample in a bath having 60 wt % $KNO_3$ and 40 wt % $NaNO_3$ at 390° C. for 3 hours.

As is known in the art, the fringes or mode lines 52TM and 52TE in the mode spectrum can be used to calculate surface compression or "compressive stress" CS and depth of layer DOL associated with an ion-exchange layer that forms an optical waveguide. In the present example, the mode spectrum 50 was obtained using a commercially available prism-coupling system, namely the FSM6000L surface stress meter ("FSM system"), available from Luceo Co., Ltd. of Tokyo, Japan. Example prism-coupling systems suitable for use for carrying out the methods disclosed herein are also described in U.S. Patent Applications No. 2014/0368808 and 2015/0066393, which are incorporated by reference herein.

The measured values of CS and DOL were 575 MPa and 4.5 microns, respectively. These are the parameters of the K+ enriched layer or spike region R1 adjacent sample surface 22. The auxiliary vertical dashed lines on the left hand side of the spectrum were added to FIG. 3 and show positions in the spectrum in which the conventional FSM system assigns to correspond to the surface index, one for TM, and one for TE. The difference in these positions is proportional to the surface compressive stress CS, which is denoted "$CS_{tot}$" in FIG. 3 to indicate the total or maximum amount of surface stress. These positions are also used in the calculation of DOL.

The present inventors have recognized that in the mode spectrum 50 for a chemically strengthened Li-containing glass having undergone a Li+ ⇔ K+, Na+ ion exchange, the position of transition from the bright to the dark portion of the spectrum, observed after the last fringe 52 in the spectrum that corresponds to the highest-order guided mode, is shifted in the TE spectrum 50TE as compared to the TM spectrum 50TM. This shift is proportional to the compressive stress CS at the depth at which the K+ concentration in spike region R1 decreases approximately to the constant-level concentration originally in the substrate (e.g., the spatially constant concentration in the glass matrix that makes up substrate body 21). The effective index of the transition corresponds to the effective index that occurs at the depth of a characteristic "knee" or transition in the stress profile, and the shift of the transition between the TE and TM spectra is proportional to the compressive stress $CS_{knee}$ at the depth of the knee (i.e., at the depth of the spike D1=$DOL_{sp}$).

The measurements of the mode spectrum 50 provided by the K+ penetration resulting from ion exchange, along with the shift in the intensity transition (e.g., transition from total internal reflection (TIR) to partial reflection as defined by the critical reflection angle in the prism-coupler system used), can be combined and used for effective quality control of a family of stress profiles that provide superior resistance to fracture. The profiles of this family are similar in shape to a power-law profile (region R2) with a spike (region R1). The spike is small in thickness when compared to the substrate thickness T. For example, the spike may be 10 microns deep (i.e., $DOL_{sp}$=10 microns), while the substrate may be T=800 microns thick. The spike may have a shape similar to a complementary error function (erfc) shape, but may also be similar to a linear depth distribution, Gaussian depth distribution, or another distribution. The main features of the spike are that it is a relatively shallow distribution and it provides substantial increase of surface compression over the level of compression at the bottom of the spike as defined by $DOL_{sp}$.

Figure 4:
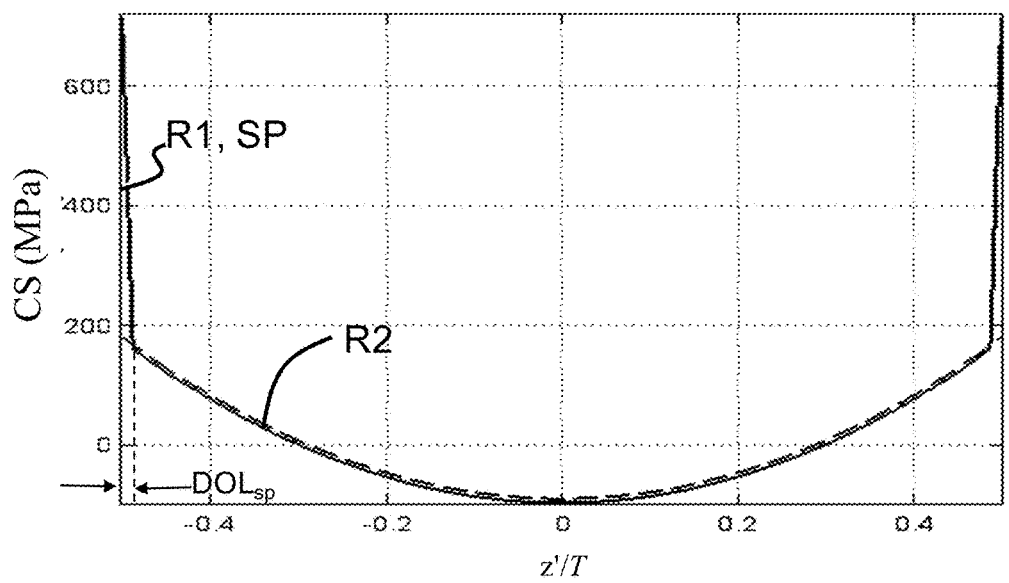
FIG. 4 is a plot of the compressive stress CS (MPa) versus a normalized position coordinate z/T, showing the model stress profile (solid line) for a sample chemically strengthened Li-containing glass that has undergone a K+ and Na+ ion exchange, wherein the dashed line represents the model profile for Na+ diffusion only, noting that the model profile has ion exchange taking place at two surfaces that respectively reside at z/T=−0.5 and +0.5.

FIG. 4 is a plot of the compressive stress CS (MPa) versus a normalized position coordinate z/T, showing the model stress profile (solid) for a sample chemically strengthened Li-containing glass that has undergone a K+ and Na+ ion exchange, wherein the dashed line represents the model profile for Na+ diffusion only (note that the model profile has ion exchange taking place at two surfaces that respectively reside at z/T=−0.5 and +0.5). The profile has a parabolic deep portion or region R2 and a surface spike portion or region (or just "spike") R1.

In the present disclosure, the assumed convention is that compressive stress CS is positive and tensile stress is negative. The model profile of FIG. 4 has a linear spike R1 added on top of a deep quadratic profile R2. Another feature of the spike is also recognized from FIG. 4, namely that the typical slope of the stress distribution in the spike R1 is significantly higher than the typical slope in the deep portion R2 of the profile, which is assumed to follow a power law, and can be approximated as parabolic for the purposes of making measurements that can be used for quality control.

The profiles that are adequately approximated as parabolic for the purposes of the quality-control measurement method of the present disclosure have a distribution of Na+ ions such that over the range of depths from the bottom of the spike to the center of the thickness (i.e., from z=$DOL_{sp}$ to T/2), the minimum Na+ concentration is at the center of the thickness (i.e., at x/L=0 in FIG. 4), and the increase in concentration at the bottom of the spike relative to the minimum concentration at the center of thickness is approximately 3 to 7 times higher than the increase in concentration at a depth equal to one quarter of the thickness, i.e., T/4. In some cases, the increase in Na+ concentration anywhere within the depth of the spike relative to the concentration in the center of the substrate may be 3 to 7 times higher than the increase in Na+ concentration (relative to the center concentration) at depth equal to one quarter of the thickness.

In one embodiment of the method, the compressive stress $CS_{knee}$ and the depth of the spike $DOL_{sp}$ are measured using a conventional prism-coupling measurement, e.g., using the aforementioned FSM system. Then a CT contribution of the spike $CT_{SP}$ is calculated using the equation:

$$CT_{sp} = \frac{CS_{SP} \times DOL_{sp}}{T - DOL_{sp}}$$

where T is the aforementioned sample thickness. The contribution to center tension of the Na+ profile $CT_{par}$, which is assumed parabolic, is calculated as:

$$CT_{par} \approx |0.5\sigma_{knee}|$$

where $\sigma_{knee}$ is the tensile stress at the knee of the profile, e.g., at the bottom of the spike and is given by:

$$\sigma_{knee} = \frac{(n_{crit}^{TE} - n_{crit}^{TM})}{SOC}$$

where $n_{crit}^{TE}$ and $n_{crit}^{TM}$ are the effective indices of the critical-angle intensity transitions as illustrated in FIG. 1. SOC is the stress-optic coefficient. Note that since tensile stress is the opposite (or negative of compressive stress, $-\sigma_{knee}=CS_{knee}$, so that the magnitude of these two quantities is the same.

As illustrated by the dashed line of FIG. 2, the assumed power-law profile may be considered as an auxiliary profile that does not include the spike and that extends the profile shape all the way to the surface of the sample. This auxiliary profile is force-balanced, having its own CT, and is hence shifted vertically from the power-law portion of the model spiked power-law profile. The auxiliary profile has a compression depth is given by $$DOC_{par} = 0.5T\left(1 - \frac{1}{\sqrt{3}}\right) \approx 0.2113T$$

The total center tension equals the sum of the contributions of the spike and of the power-law portion:

$$CT_{tot} = CT_{par} + CT_{sp}.$$

The depth of compression DOC of the spiked power-law profile can be calculated by using the expression:

$$DOC = 0.5T\left(1 - \sqrt{\frac{CT_{tot}}{3CT_{par}}}\right) = 0.5T\left(1 - \sqrt{\frac{1}{3}\left(1 + \frac{CT_{sp}}{CT_{par}}\right)}\right) \approx$$

$$DOC_{par}\left(1 - \frac{CT_{sp}}{2CT_{par}(\sqrt{3}-1)}\right) \approx DOC_{par} - \frac{0.5T}{\sqrt{3}}\frac{CT_{sp}}{2CT_{par}}$$

The approximate expressions at the end of the above equation are valid when the CT contribution of the spike is significantly smaller than the CT contribution of the auxiliary power-law profile.

In summary, the above-described method includes: 1) measuring the mode spectrum due to the spike and estimating a contribution of the spike to the center tension; 2) using the mode spectrum, measuring the shift of the critical angle; 3) estimating a compression at the knee, which is proportional to the contributions of the substantially power-law profile and of the spike.

In addition, a compression depth DOC of the profile may be estimated by using an exact formula for the model profile, or an approximate formula that gives the DOC as the DOC of an auxiliary power-law profile (e.g., parabolic or nearly parabolic) less a small DOC reduction due to the spike.

Furthermore, in one example embodiment, the depth of spike $DOL_{sp}$ is used to verify that the deep portion of the profile (region R2) is in a regime well represented by the power-law profile shape. In particular, as the $DOL_{sp}$ of the spike increases, the penetration of Na+ increases approximately in proportion to the $DOL_{sp}$ of the spike. Hence, for a glass where simultaneous in-diffusion of K+ and Na+ is used, a minimum $DOL_{sp}$ can be set for any particular glass thickness, above which the deep portion of the profile can be considered to follow a power law. In another example, an upper limit of the $DOL_{sp}$ may also be imposed to exclude physical profiles that start to deviate substantially from the parabolic model as a result of stress relaxation, which may become prominent at very long ion exchange times at high temperature.

The above-described method is a somewhat simplified version of a more precise method. The simplification incurs only a minor error when the CT contribution of the spike is much smaller than the CT contribution of the auxiliary power-law profile. The CT contribution of the spike shifts the power-law portion vertically by the amount $CT_{sp}$ relative to the auxiliary power-law profile. As a result, the compression at the knee of the model spiked profile is actually smaller than the compression of the auxiliary profile at the knee depth by the amount $CT_{sp}$.

Furthermore, there is a minor change in compression of the auxiliary power-law profile between the surface and the depth of the knee, and, for a force-balanced power-law profile the CT is actually equal to half of the surface compression.

The following steps represent an example of a more precise method for determining the parameters of the model spiked power-law profile from the prism-coupling measurements:

a) Calculate preliminary $$CT_{sp}^{(0)} = \frac{(CS_{tot} - CS_{knee}) \times DOL_{sp}}{T - DOL_{sp}}$$

b) Calculate preliminary $$CS_{par}^{(0)} = \frac{CS_{knee} + CT_{sp}^{(0)}}{1 - 6\frac{DOL_{sp}}{T} + 6\frac{DOL_{sp}^2}{T^2}}$$

c) (Optional alternative to steps 4, 5, and 6) Calculate preliminary $$CT_{par}^{(0)} = 0.5CS_{par}^{(0)} = 0.5\frac{CS_{knee} + CT_{sp}^{(0)}}{1 - 6\frac{DOL_{sp}}{T} + 6\frac{DOL_{sp}^2}{T^2}} \text{ and}$$

$$CT_{tot}^{(0)} = CT_{par}^{(0)} + CT_{sp}^{(0)}$$

d) Calculate more precise $$CT_{sp}^{(1)} = \frac{(CS_{tot} - CS_{par}^{(0)}) \times DOL_{sp}}{T - DOL_{sp}}$$

e) Calculate more precise $$CS_{par}^{(1)} = \frac{CS_{knee} + CT_{sp}^{(1)}}{1 - 6\frac{DOL_{sp}}{T} + 6\frac{DOL_{sp}^2}{T^2}}, \text{ and}$$

$$CT_{par}^{(1)} = 0.5CS_{par}^{(1)} = 0.5\frac{CS_{knee} + CT_{sp}^{(1)}}{1 - 6\frac{DOL_{sp}}{T} + 6\frac{DOL_{sp}^2}{T}}$$

f) Calculate more precise $CT_{tot}^{(1)} = CT_{par}^{(1)} + CT_{sp}^{(1)}$ g) (Optional)—Can continue iteration, finding more and more precise values for $CT_{sp}$ and $CS_{par}$ until desired level of convergence or precision. More than one iteration would rarely be of use, since actual profiles are unlikely to be precisely power law and have a precisely linear spike. More than one iteration may be useful in relatively thin substrates in which the depth of the spike may represent more than about 3% of the substrate thickness.

h) (Optional) Determine depth of compression DOC of the profile, for example using one of the forms of the equation:

$$DOC = 0.5T\left(1 - \sqrt{\frac{CT_{tot}}{3CT_{par}}}\right) = 0.5T\left(1 - \sqrt{\frac{1}{3}\left(1 + \frac{CT_{sp}}{CT_{par}}\right)}\right) \approx$$

$$DOC_{par}\left(1 - \frac{CT_{sp}}{2CT_{par}(\sqrt{3}-1)}\right) \approx DOC_{par} - \frac{0.5T}{\sqrt{3}}\frac{CT_{sp}}{2CT_{par}}$$

In the case where one is working directly with the DOL as measured by conventional means and not the real depth of layer or position of the spike, a range of approximations may be needed, some of which are empirical in nature.

In many cases, the power-law profile can be estimated as parabolic or substantially parabolic, i.e., to the power 2. In other cases, substantially nonlinear diffusion may cause the shape of the deep portion of the stress profile to be best represented by a relatively high power-law profile, e.g., to the power 3, i.e., cubic, or even higher. The methods that employ profiles greater than parabolic can can be used to improve the accuracy with which the quality-control model represents the actual stress profile, and in this way to increase the range of ion exchange conditions over which the quality control method works effectively for the particular glass of interest.

For example, for a parabolic profile the ratio of CS to CT by absolute value is 2. Similarly, for a cubic profile the corresponding ratio is 3, and for a quartic profile it is 4. A force-balanced profile representation using the power of 3/2 has a CS to CT ratio of 1.8. Note that for power-function profile where the power is not an even number, the profile is constructed as the absolute value of the power function. In the mentioned examples, the depth of compression for the non-spiked auxiliary profile is about 0.23 T for the profile with power 3/2, 0.21 T for the power-law profile, 0.185 T for the cubic profile, and 0.165 T for the quartic profile.

Once a model-profile shape is found to represent the relatively stable shape of the center-connected concentration and stress profile, the corresponding ratio of CS to CT and DOC estimate can be used for the auxiliary profile in the application of the method of the present invention for quality control.

Thus, in a more generic embodiment of the invention, the auxiliary deep portion of the spiked profile may be represented with a symmetric absolute value of a power function of the distance from the center, and an associated ratio of CS to CT of a force-balanced profile having the shape of the model function is used to estimate the CT from the measured compression at the knee or estimated compression at the surface. If the depth of compression is also sought, the depth of compression of the model profile may be used as an approximate reference, or the depth of compression of the full force-balanced model profile may be calculated as was done for the example spiked power-law profile. In an example, the ratio CS to CT ranges from about 1.8 to about 4, while the DOC for the auxiliary model profile ranges from about 0.16 T to about 0.23 T.

Figure 5:
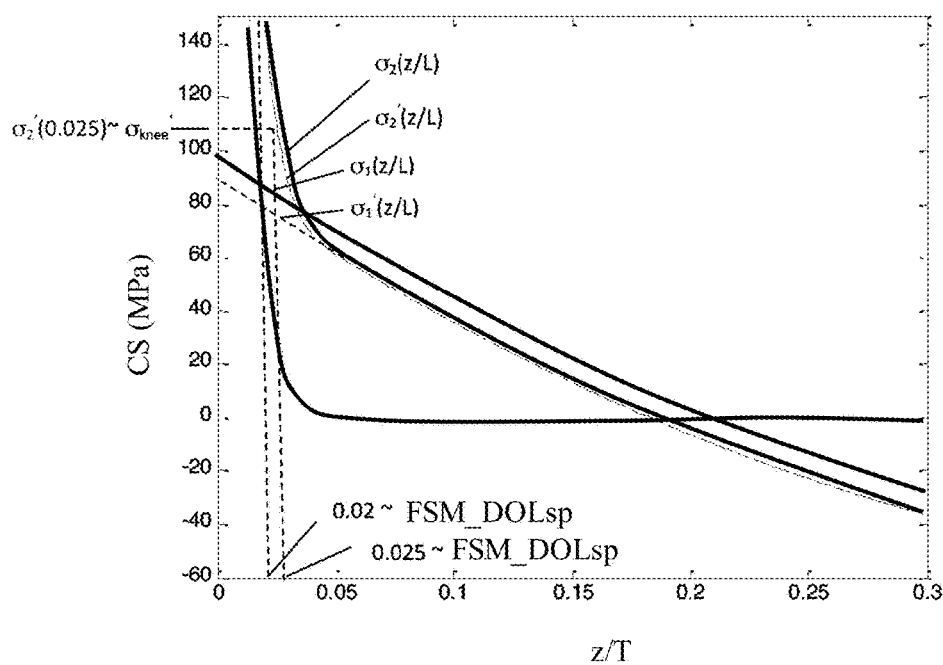
FIG. 5 is a plot of the stress (MPa) versus a normalized position coordinate z/T showing separate plots for the spike portion, the long diffused power-law portion and the spike plus power-law portion of the stress profile.

FIG. 5 is a plot of the stress (MPa) versus a normalized position coordinate x/L and shows separate plots for the spike portion, the long diffused power-law portion and the spike plus power-law portion of the stress profile. Another embodiment uses the parabolic auxiliary profile as illustrated in FIG. 4 and the following representation for the force-balanced power-law profile (the solid line):

$$\sigma_1\left(\frac{z}{L}\right) = \sigma_1(0)\left[-\frac{1}{2} + 6\left(\frac{z}{L} - 0.5\right)^2\right] \quad (1)$$

A conventional measurement (e.g., using the aforementioned FSM system) is used to measure "FSM_DOL" of the spike as approximately the diffusion depth given by $2\sqrt{D\cdot\tau}$ where D is the diffusion coefficient and τ is the time of diffusion. Then, using the fact above where ~1.25×FSM_DOL leads to most of the area of the spike to be included, one can get an approximate equation for the CT due to the spike contribution, namely $$CT_{spike} = \frac{(\sigma_2'(0) - \sigma_2'(1.25 \times \text{FSM\_DOL})) \times 1.25 \times \text{FSM\_DOL}}{T - 1.25 \times \text{FSM\_DOL}} \quad (2)$$

The point σ₂'(1.25×FSM_DOL) although not equal to is acceptably close to the CS between the transition between guided modes and continuum in the spiked lithium glass samples. This point is called the $CS_{knee}$ and is shown in FIG. 3 as a reasonable approximation. It is also reasonable to approximate the stress and the offset due to the contribution of the $CT_{spike}$ deeper inside the glass.

Since the power-law profile will be slowly varying as compared to the spike portion of the profile, it can be assumed that the stress at ~(2-3)×FSM_DOL in the power-law region would not feel the presence of the spike. It therefore follows that:

$$\sigma_1\left(\frac{z}{L}\right) \cong \sigma_1'\left(\frac{z}{L}\right) + CT_{spike} \quad (3)$$

and, $$\sigma_1\left(\frac{3 \times \text{FSM\_DOL}}{L}\right) \cong \sigma_1'\left(\frac{3 \times \text{FSM\_DOL}}{L}\right) + CT_{spike} \quad (4)$$

Using the parabolic power-law equation in (1), one establish the following relationships:

$$\sigma_1\left(\frac{3 \times \text{FSM\_DOL}}{L}\right) = \sigma_1(0)\left[-\frac{1}{2} + 6\left(\frac{3 \times \text{FSM\_DOL}}{L} - 0.5\right)^2\right] \cong \quad (5)$$

$$\sigma_1'\left(\frac{3 \times \text{FSM\_DOL}}{L}\right) + CT_{spike} \text{ and}$$

$$\sigma_1(0) \cong \frac{\sigma_1'\left(\frac{3 \times \text{FSM\_DOL}}{L}\right) + CT_{spike}}{\left[-\frac{1}{2} + 6\left(\frac{3 \times \text{FSM\_DOL}}{L} - 0.5\right)^2\right]} \quad (6)$$

Numerically it can be demonstrated that if one uses a factor 2 instead of 3, the results are almost the same, in some cases varying by just 1%-2% of σ₁(0). Therefore, if one can find the approximated value of $$\sigma_1'\left(\frac{3 \times \text{FSM\_DOL}}{L}\right) \text{ or } \sigma_1'\left(\frac{2 \times \text{FSM\_DOL}}{L}\right)$$

in the FSM, one can use equation (6) to compute the original stress of the first stress parabola within this range of error.

In practice one can measure approximately $$\sim \sigma_1'\left(\frac{3 \times \text{FSM\_DOL}}{L}\right) \text{ to } \sim \sigma_1'\left(\frac{2 \times \text{FSM\_DOL}}{L}\right)$$

by examining the stress generated at the transition between guided modes and continuum in the spike on Li-glass samples. This point where approximately $$\sim \sigma_1'\left(\frac{3 \times \text{FSM\_DOL}}{L}\right) \text{ to } \sim \sigma_1'\left(\frac{2 \times \text{FSM\_DOL}}{L}\right)$$

can be used as the point $CS_{knee}$ as shown in FIG. 3 as a reasonable approximation that can be measured by computing the distance between these lines (fringes) in TM and TE spectra and their refractive index. In light of the stress optical coefficient (SOC) of the material the division of the index difference at this point per the SOC would lead to the $CS_{knee}$ stress values.

This is in addition to the FSM_DOL and the $CS \sim \sigma_2'(0)$ given by the FSM for the spike. Therefore $CT_{parabola} = CT_{par} \sim \sigma_1(0)/2$, and $CT_{spike}$ is given in (2) as (repeated for convenience)

$$CT_{spike} = \frac{(\sigma_2'(0) - \sigma_2'(1.25 \times \text{FSM\_DOL})) \times 1.25 \times \text{FSM\_DOL}}{T - 1.25 \times \text{FSM\_DOL}} \quad (2)$$

From there, one can (repeating the previous equations) then compute the total center tension equals the sum of the contributions of the spike and of the power-law portion:

$$CT_{tot} = CT_{par} + CT_{spike} \quad (7)$$

If desired the depth of compression of the spiked power-law profile can be calculated/estimated by using the expression:

$$DOCtotal = 0.5T\left(1 - \sqrt{\frac{CT_{tot}}{3CT_{par}}}\right) = 0.5T\left(1 - \sqrt{\frac{1}{3}\left(1 + \frac{CT_{sp}}{CT_{par}}\right)}\right) \approx \quad (2)$$

$$DOC_{par}\left(1 - \frac{CT_{sp}}{2CT_{par}(\sqrt{3}-1)}\right) \approx DOC_{par} - \frac{0.5T}{\sqrt{3}}\frac{CT_{sp}}{2CT_{par}}$$

These equations assume that the deep part of the profile is approximately parabolic in nature and has an added spike near the surface. Its validity is better matched when the spike is small in stress amplitude and not so deep in comparison to the deeper power-law portion of the profile.

Figure 6:
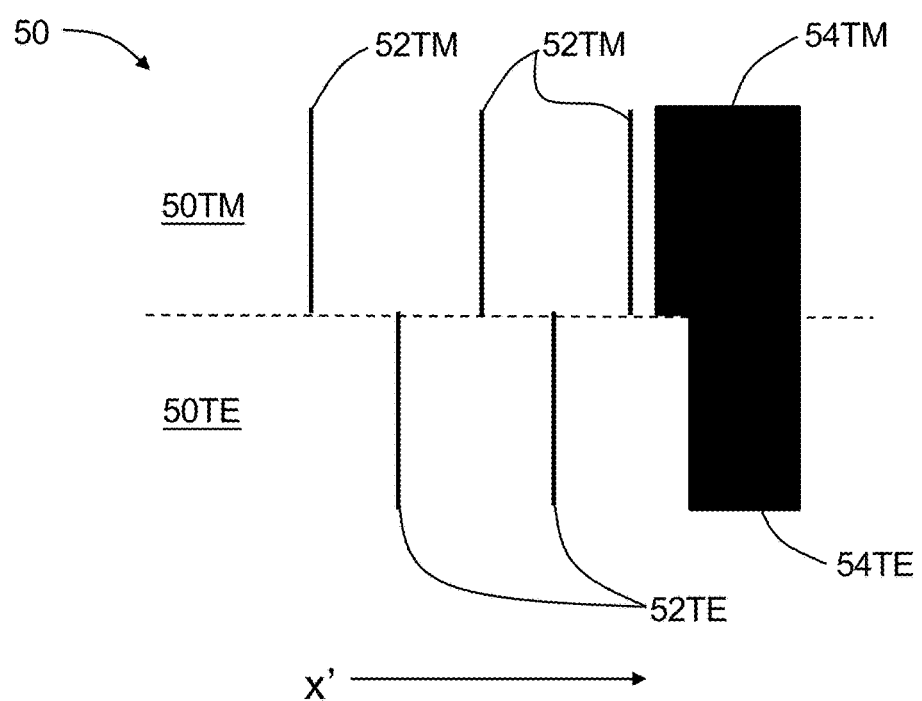
FIG. 6 is a schematic representation of a measured mode spectrum showing the TE and TM mode spectra for an example chemically strengthened Li-containing glass sample.
Figure 7A:
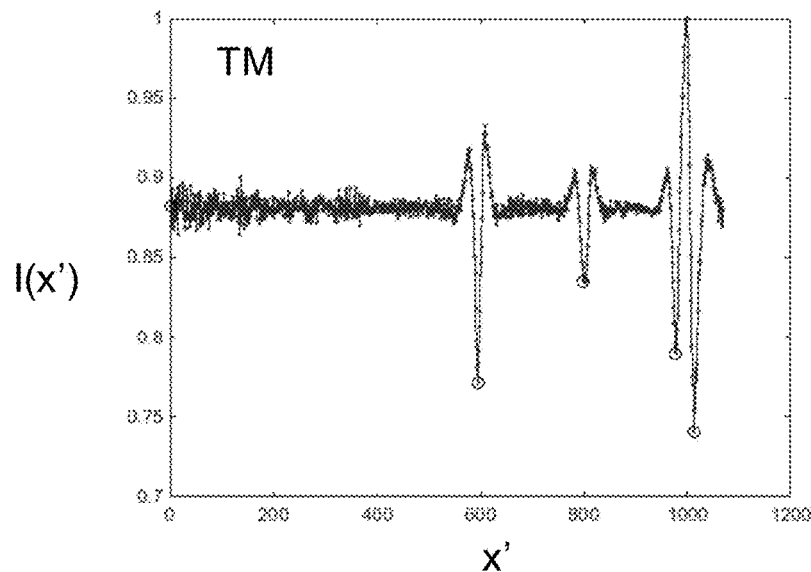
FIGS. 7A and 7B are plots of the intensity I versus distance x' along the mode spectrum for the mode lines or fringes of TE and TM mode spectra, respectively, of FIG. 6.
Figure 7B:
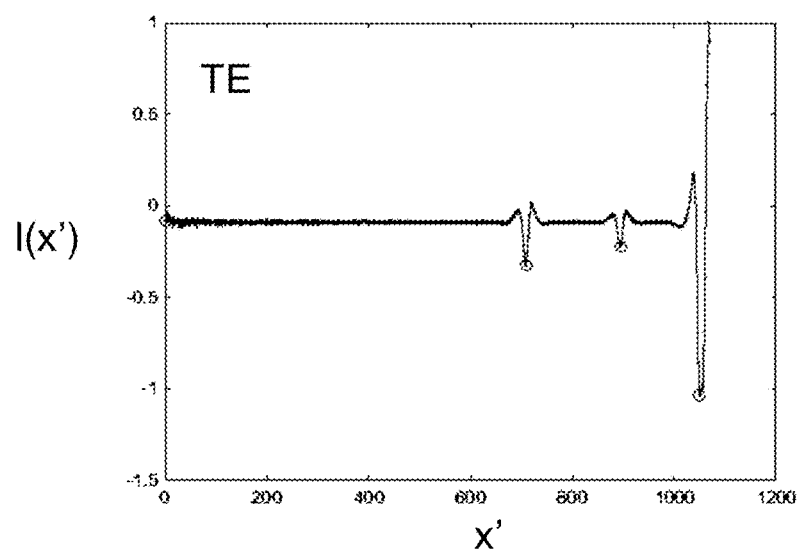

An aspect of the disclosure is the use the algorithm described by the above equations to process measured mode spectra. FIG. 6 is a schematic representation of a measured mode spectrum showing the TE and TM mode spectra based on actual measured mode spectra for an example chemically strengthened Li-containing glass sample. In this case using the algorithm above considering that both $\sigma_2'(1.25 \times \text{FSM\_DOL}) \sim CS_{knee}$ and that $$\sigma_1'\left(\frac{3 \times \text{FSM\_DOL}}{L}\right) \sim CS_{knee}$$

as reasonable approximations, one can find that:
FSM_DOL=$DOL_{sp}$=7.77 um
$\sigma_2'(0)$=CSspike=482.6 MPa
$CS_{knee}$=138.8 MPa
$CT_{spike}$=4.23 MPa
$CS_{parabola}$=$\sigma_1'(0)$=172.3 MPa
$CT_{parabola}$=86.14 MPa
$CT_{total}$=90.4 MPa
$DOC_{parabola}$=169 um
$DOC_{total}$=163.4 um The method of measurement of the compression at the knee as described above has some accuracy limitations. For any particular measurement wavelength, there are certain quasi-periodic ranges of the spike DOL within which the accuracy of the measurement of the critical-angle shift is reduced. The cause of this reduction is the appearance of a leaky mode with an effective index close to that of the critical angle as the DOL is increased from a range where the critical-angle transition is clear-cut.

In the example of FIG. 3, the signature of such a leaky mode can be observed in the TM mode spectrum as the extra-dark relatively narrow band immediately on the right-hand-side of the transition from bright to dark. When the leaky mode has an effective index very close to the critical-angle index, the shape of the critical-angle transition is changed by the leaky mode, resulting in error in the measurement of the shift. When a leaky mode affects only the critical-angle transition for the TM spectrum, the compression at the knee is slightly over-estimated. When it affects only the critical-angle transition for the TE spectrum, the compression at the knee is slightly under-estimated. When a leaky mode affects both the TM and the TE transition, the net error of the compression at the knee could be positive or negative, and smaller as compared to the error when the transition for only one polarization is substantially affected.

Consequently, aspects of the measurement methods disclosed herein are directed to eliminate or mitigate the error in the measurement of the knee compression that is caused by the presence of a leaky mode. In one embodiment, the target $DOL_{sp}$ is selected such that the effective index of a leaky mode is not close to the critical-angle transition, neither for the TM nor for the IL polarization. If such a choice of $DOL_{sp}$ is not available within the range of preferable overall product stress-profile designs, then the measurement wavelength is chosen such that a leaky mode at the measurement wavelength is not close to the critical angle at either polarization. The way the DOL is measured traditionally is by assigning a fraction of a mode to the index range between the highest-order guided mode and the critical angle for the purposes of mode counting, to provide a continuous measured DOL as a function of increasing diffusion depth by using a continuously varying number of modes.

The equation for the DOL is:

$$DOL = \frac{(2N - 0.5)\lambda}{3.77\sqrt{n\Delta n}}$$

where n is the approximate average index of the measured waveguiding layer, and $\Delta n$ is the difference between the maximum and minimum index of the waveguide assumed to have a truncated linear profile. In the case of the measurement of the spike, $\Delta n$ refers to the difference between the surface index and the index at the knee of the stress profile. N is the continuous number of modes. In the example of FIG. 3, N is approximately 2.6 modes for the TM spectrum and 2.4 modes for the TE spectrum.

The condition for selecting a preferred target DOL or a preferred measurement wavelength is that the non-integer part of the number of modes N be between about 0.1 and 0.6 at both the TM and TE polarization. Hence, in one embodiment of the invention, the measurement wavelength and the depth of the spike are such that the non-integer part of the number of modes is between about 0.1 and 0.6 at both polarizations, preferably between 0.2 and 0.55.

In another less restrictive embodiment, a correction for the effect of the leaky mode is made during the interpretation of the measured shift of the critical transition. The non-integer part of each of the TM and TE number of modes is taken into account, and a correction is made that accounts effect of the leaky mode. To this end, a calibration of the effect of the leaky mode of each polarization on the measured knee compression may be used. In an example, a sequence of samples having $DOL_{sp}$ increasing in small steps is fabricated in the same salt mixture and at the same temperature, and used for the calibration. The actual compression at the knee decreases monotonically and smoothly with increasing $DOL_{sp}$, while the estimated compression fluctuates above and below the smooth dependence of the actual compression on $DOL_{sp}$ as a result of the error induced by the leaky mode. By tracking the dependence of the fluctuation on the non-integer part of the TM and TE mode numbers, the calibration of the necessary correction is obtained.

In another embodiment, the intensity profile in the vicinity of the critical angle is analyzed, the contribution of the leaky mode is estimated based on the shape of the intensity profile and the non-integer mode number, and the estimated contribution is corrected for in the intensity profile to calculate a more accurate position of the critical angle. This is done independently for the TM and the TE polarization, and the stress at the knee is estimated after the TM and TE critical angles are found following the application of the intensity corrections.

In another embodiment, the weight gain of a sample as a result of ion exchange is used in combination with the prism-coupling measurement. The weight gain may be used to verify that enough Na ions have exchanged for Li ions such that the use of the power-law profile model is valid for quality control. For the purpose, a target acceptable weight gain range is prescribed for the ion exchange based on the total surface area of the sample and the sample thickness. The weight of representative samples is measured before and after ion exchange, and the quality-control prism-coupling measurements are considered valid if the measured weight gain per sample falls in the target range.

In another embodiment of the method, advantage is taken of the precise control of the sample shape, and of individual-sample thickness measurements that are common in some production processes. In this case it is possible to verify that the sample has had adequate weight gain by simply measuring the sample thickness with high precision (such as +/−2 microns), and measuring the post-ion exchange weight of the sample. From the known shape specification, the measured thickness, and the known density of the pre-ion-exchanged glass, the weight of the pre-ion-exchanged sample is calculated. A correction factor may be applied that accounts for a typical volume change as a result of ion exchange. The weight gain then is estimated by subtracting from the measured post-ion-exchange weight the estimated pre-exchanged weight. If the weight gain falls within the target range, the profile is deemed adequately represented by the quality-control model profile, and the prism-coupling QC measurement is considered valid.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A method of improving functionality of a prism-coupling system to measure a center tension CT in a chemically strengthened Li-containing glass sample having a body with a thickness T, and a spike region and a deep region within the body, and a surface defined by the body, comprising:
   a) performing an ion-exchange process that exchanges Li+ ions in the glass sample with Na+ and K+ ions, wherein the K+ ions and Na+ ions define a stress profile that includes the spike region in the body adjacent the surface and defined substantially by the K+ ions and the deep region that extends from a bottom of the spike region into the glass body and defined substantially by the Na+ ions, wherein the spike region and the deep region are joined at a knee having a knee depth $DOL_{sp}$;
   b) measuring a mode spectrum of the glass sample using the prism-coupling system;
   c) estimating from the mode spectrum: i) a surface compressive stress $CS_{sp}$ produced by the spike region; ii) a spike center tension $CT_{sp}$ for the spike region only using the relationship $CT_{sp}=[CS_{sp} \times DOL_{sp}]/[T-DOL_{sp}]$; iii) a knee stress $CS_{knee}$ at the knee and iv) a deep region center tension $CT_{par}$ as produced by the deep region only using the knee stress $CS_{knee}$ and a parabolic profile approximation for the deep region center tension $CT_{par}$;
   d) estimating the center tension CT of the glass sample by the relationship $CT_{sp}+CT_{par}$.

2. The method according to claim 1, further comprising performing quality control of the formation of chemically strengthened Li-containing glass samples by:
   forming multiple chemically strengthened Li-containing glass samples according to act a);
   performing acts b) through d) to non-destructively measure the center tension of at least one of the multiple glass samples; and
   adjusting act a) for subsequent glass samples so that the estimated center tension CT falls within a center tension specification for the subsequent glass samples.

3. The method according to claim 1, wherein the deep region center tension $CT_{par} \approx |0.5\sigma_{knee}|$.

4. The method according to claim 1, wherein acts c) and d) are carried out in a processor of the prism-coupling system using instructions embodied in a non-transitory computer-readable medium that controls the processor.

5. A method of improving functionality of a prism-coupling system having a controller to measure a center tension in a chemically strengthened Li-containing glass sample having a surface and a body and a stress profile formed by an exchange of Li ions with Na+ and K+ ions, wherein the stress profile includes a spike region adjacent the sample surface and deep region that extends from a bottom of the spike region into the glass body, the method comprising:
   a) measuring a mode spectrum of the glass sample using the prism-coupling system;

b) using the controller, estimating from the mode spectrum a first contribution to the center tension associated with the spike region and estimating a second contribution to the center tension due to the deep region only, wherein the deep region is assumed to follow a power-law stress profile; and c) estimating a total center tension by adding in the controller the first and second contributions to the center tension.

6. The method according to claim 5, further comprising performing quality control of the formation of chemically strengthened Li-containing glass samples by:

forming multiple chemically strengthened Li-containing glass samples;

performing acts b) and c) to non-destructively measure the center tension of the multiple glass samples; and adjusting the forming of subsequent glass samples so that the estimated center tension of the subsequent glass samples falls within a center tension specification.

7. The method according to claim 5, wherein the power-law stress profile is substantially parabolic.

8. The method according to claim 5, wherein the substrate has a thickness T, the spike region has a surface compressive stress CS, and the spike region and the deep region are joined at a knee having a knee depth $DOL_{sp}$, and wherein:

the first contribution to the center tension is defined by a spike center tension defined by $CT_{sp} = [CS_{sp} \times DOL_{sp}]/[T-DOL_{sp}]$.

9. The method according to claim 8, wherein the knee has a knee stress $CS_{knee}$ and the second contribution to the center tension is a deep region center tension $CT_{par}$ defined by $CT_{par} \approx |0.5\sigma_{knee}|$.

10. A method of improving a process for forming chemically strengthened glass samples, comprising:

a) forming a chemically strengthened first glass sample using an ion-exchange (IOX process), the first glass sample having a body, a surface and a stress profile that includes a spike region adjacent the sample surface and a deep region that extends from a bottom of the spike region into the body;

b) measuring a mode spectrum of the first glass sample using a prism-coupling system having a controller;

c) using the controller, estimating from the mode spectrum a first center tension for the spike region only and estimating a second center tension for the deep region only, including assuming a power-law stress profile for the deep region;

d) estimating in the controller a total center tension CT for the first glass sample by adding the first and second center tensions;

e) comparing in the controller the determined center tension CT of act c) to a center tension specification; and f) adjusting the IOX process and forming a second chemically strengthened glass sample based on the act e) of comparing of the determined center tension CT to the center tension specification for the chemically strengthened first glass sample.

11. The method according to claim 10, wherein the power-law stress profile is substantially parabolic.

12. The method according to claim 10, wherein stress profile is formed using an ion-exchange of Li+ ions in the glass with K+ and Na+ ions.

13. The method according to claim 12, wherein the act e) of adjusting comprises changing at least one of: a concentration of K+ ions, a concentration of Na+ ions, a diffusion temperature and a diffusion time.

14. The method according to claim 10, wherein measuring the mode spectrum includes capturing the mode spectrum on a photodetector of the prism-coupling system.

15. The method according to claim 10, further including measuring at least one additional stress-related characteristic of the glass sample.

16. The method according to claim 10, wherein the substrate has a thickness T, the spike region has a surface compressive stress CS, and the spike region and the deep region are joined at a knee having a knee depth $DOL_{sp}$, and wherein:

the first contribution to the center tension is defined by a spike center tension defined by $CT_{sp} = [CS_{sp} \times DOL_{sp}]/[T-DOL_{sp}]$.

17. The method according to claim 16, wherein the knee has a knee stress $CS_{knee}$ and the second contribution to the center tension is a deep region center tension $CT_{par}$ defined by $CT_{par} \approx |0.5\sigma_{knee}|$.

* * * * *

UNITED STATES PATENT AND TRADEMARK OFFICE
CERTIFICATE OF CORRECTION

PATENT NO. : 10,180,416 B2
APPLICATION NO. : 15/171490
DATED : January 15, 2019
INVENTOR(S) : Rostislav Vatchev Roussev et al.

It is certified that error appears in the above-identified patent and that said Letters Patent is hereby corrected as shown below:

In the Claims

In Column 14, Line 24, Claim 1, before "body" delete "glass".

In Column 14, Line 52, Claim 3, delete "$|0.5\sigma_{knee}|$." and insert -- $|0.5CS_{knee}|$. --, therefor.

In Column 14, Line 64, Claim 5, before "body," delete "glass".

In Column 15, Line 32, Claim 9, delete "$|0.5\sigma_{knee}|$." and insert -- $|0.5CS_{knee}|$. --, therefor.

In Column 16, Line 43, Claim 17, delete "$|0.5\sigma_{knee}|$." and insert -- $|0.5CS_{knee}|$. --, therefor.

Signed and Sealed this
Sixth Day of August, 2019

Andrei Iancu
*Director of the United States Patent and Trademark Office*